US012600737B2

(12) United States Patent
Herzog et al.

(10) Patent No.: US 12,600,737 B2
(45) Date of Patent: Apr. 14, 2026

(54) BIDENTATE PHOSPHITE LIGANDS, CATALYTIC COMPOSITIONS CONTAINING SUCH LIGANDS, AND CATALYTIC PROCESSES UTILIZING SUCH CATALYTIC COMPOSITIONS

(71) Applicant: INV NYLON CHEMICALS AMERICAS, LLC, Wilmington, DE (US)

(72) Inventors: Benjamin David Herzog, Wichita, KS (US); William J. Tenn, III, Beaumont, TX (US)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 0 days.

(21) Appl. No.: 18/995,170

(22) PCT Filed: Jul. 28, 2023

(86) PCT No.: PCT/IB2023/057677
§ 371 (c)(1),
(2) Date: Jan. 16, 2025

(87) PCT Pub. No.: WO2024/028722
PCT Pub. Date: Feb. 8, 2024

(65) Prior Publication Data

US 2026/0015370 A1 Jan. 15, 2026

Related U.S. Application Data

(60) Provisional application No. 63/394,315, filed on Aug. 2, 2022.

(30) Foreign Application Priority Data

Oct. 13, 2022 (GB) ..................................... 2215077

(51) Int. Cl.
*C07F 9/145* (2006.01)
*C07C 253/10* (2006.01)
*C07F 15/04* (2006.01)

(52) U.S. Cl.
CPC ............ *C07F 9/145* (2013.01); *C07C 253/10* (2013.01); *C07F 15/04* (2013.01)

(58) Field of Classification Search
CPC ......... C07F 9/145; C07F 15/04; C07C 253/10
See application file for complete search history.

(56) References Cited

U.S. PATENT DOCUMENTS 3,496,217 A 2/1970 Drinkard, Jr.
3,496,218 A 2/1970 Drinkard, Jr.
3,631,191 A 12/1971 Kane
3,655,723 A 4/1972 Drinkard, Jr.
3,846,461 A 11/1974 Shook
3,847,959 A 11/1974 Shook
3,903,120 A 9/1975 Shook, Jr.
4,467,116 A 8/1984 Van Leeuwen et al.
4,774,353 A 9/1988 Hall
4,874,884 A 10/1989 Mckinney
5,512,696 A 4/1996 Kreutzer
5,663,369 A 9/1997 Kreutzer
5,688,986 A 11/1997 Tam
5,717,126 A 2/1998 Paciello et al.
5,723,641 A 3/1998 Tam
5,821,378 A 10/1998 Foo
5,847,191 A 12/1998 Bunel
5,910,600 A 6/1999 Urata
6,121,184 A * 9/2000 Druliner ............... C07C 253/10 502/166
6,812,352 B2 11/2004 Kreutzer et al.
6,852,661 B1 2/2005 Ahlers et al.
7,531,693 B2 5/2009 Gebeyehu et al.
7,906,688 B2 3/2011 Brammer et al.
9,011,691 B2 4/2015 Tenn et al.
9,040,733 B2 5/2015 Moerbe et al.
9,040,735 B2 5/2015 Aki et al.
9,050,591 B2 6/2015 Fraga-dubreuil
9,221,852 B2 12/2015 Forsyth
9,932,298 B2 4/2018 Vos
10,143,999 B2 12/2018 Fraga-dubreuil et al.
10,537,885 B2 1/2020 Medhekar
10,759,741 B2 9/2020 Aki et al.
(Continued)

FOREIGN PATENT DOCUMENTS

DE 102005061642 A1 7/2006
EP 1344770 A1 9/2003
(Continued)

OTHER PUBLICATIONS

Bugerenko et al., "Structure of reaction products of alkylhalosilanes with sodium dialkyl phosphites", Zhumal Obshchei Khimii, 2023, 1 page (Abstract Only).
Chivers et al., "Lithiation of Tris(alkyl- and arylamido)orthophosphates EP[N(H)R]3(E ) O, S, Se): Imido Substituent Effects and PdE Bond Cleavage", Inorganic Chemistry, vol. 42, No. 13, 2003, pp. 3994-4005.
Das et al., "Carbohydrate recognition: Enantioselective spirobifluorene diphosphonate receptors", Tetrahedron Letters, vol. 38, Issue 21, May 26, 1997, pp. 3675-3678.
(Continued)

*Primary Examiner* — James H Alstrum-Acevedo
*Assistant Examiner* — Manahil Mirghani Ali Abdalhameed

(57) ABSTRACT

A bidentate phosphite ligand comprises a backbone having a structure of acenaphthene-1,2-diol in which the hydrogen atoms of the hydroxyl groups have each been replaced by a $P(OR^1)_2$ group, where $R^1$ is an aryl radical. When combined with a transition metal, such as nickel, the ligand provides a catalyst complex useful in hydrocyanation and other reactions.

18 Claims, 1 Drawing Sheet

(56) References Cited

U.S. PATENT DOCUMENTS

| | | | |
|---|---|---|---|
| 2003/0135014 | A1 | 7/2003 | Radu et al. |
| 2003/0144440 | A1 | 7/2003 | Gagne et al. |
| 2003/0144559 | A1 | 7/2003 | Hess et al. |
| 2006/0052624 | A1 | 3/2006 | Galland et al. |
| 2006/0100455 | A1 | 5/2006 | Galland et al. |
| 2022/0242891 | A1 | 8/2022 | Zhang |

FOREIGN PATENT DOCUMENTS

| | | | |
|---|---|---|---|
| EP | 2243763 | B1 | 10/2014 |
| GB | 1417554 | A | 12/1975 |
| JP | 2007203269 | A | 8/2007 |
| KR | 20220025310 | A | 3/2022 |
| WO | 9514659 | A1 | 6/1995 |
| WO | 9906146 | A2 | 2/1999 |
| WO | 9906357 | A1 | 2/1999 |
| WO | 9952632 | A1 | 10/1999 |
| WO | 0134612 | A2 | 5/2001 |
| WO | 0240491 | A1 | 5/2002 |
| WO | 2004007435 | A2 | 1/2004 |
| WO | 2004024684 | A2 | 3/2004 |
| WO | 2004050588 | A2 | 6/2004 |
| WO | 2012033556 | A1 | 3/2012 |
| WO | 2013181095 | A1 | 12/2013 |

OTHER PUBLICATIONS

Harold Hart, "Iptycenes, cuppedophanes and cappedopha", Department of Chemistry, Michigan State University, Pure & Applied Chern., vol. 65, No. 1, 1993, pp. 27-34.

International Preliminary Report on Patentability received for PCT Application No. PCT/IB2023/055290, mailed on Dec. 5, 2024, 6 pages.

International Preliminary Report on Patentability received for PCT Application No. PCT/IB2023/055292, mailed on Dec. 5, 2024, 7 pages.

International Preliminary Report on Patentability received for PCT Application No. PCT/IB2023/057665, mailed on Feb. 13, 2025, 8 pages.

International Preliminary Report on Patentability received for PCT Application No. PCT/IB2023/057666, mailed on Feb. 13, 2025, 7 pages.

International Preliminary Report on Patentability received for PCT Application No. PCT/IB2023/057667, mailed on Feb. 13, 2025, 9 pages.

International Preliminary Report on Patentability received for PCT Application No. PCT/IB2023/057668, mailed on Feb. 13, 2025, 11 pages.

International Preliminary Report on Patentability received for PCT Application No. PCT/IB2023/057673, mailed on Feb. 13, 2025, 7 pages.

International Preliminary Report on Patentability received for PCT Application No. PCT/IB2023/057675, mailed on Feb. 13, 2025, 11 pages.

International Preliminary Report on Patentability received for PCT Application No. PCT/IB2023/057677, mailed on Feb. 13, 2025, 7 pages.

International Search Report and Written Opinion received for PCT Application No. PCT/IB2023/055290, mailed on Aug. 29, 2023, 7 pages.

International Search Report and Written Opinion received for PCT Application No. PCT/IB2023/055292, mailed on Aug. 29, 2023, 9 pages.

International Search Report and Written Opinion received for PCT Application No. PCT/IB2023/057665, mailed on Nov. 7, 2023, 11 pages.

International Search Report and Written Opinion received for PCT Application No. PCT/IB2023/057666, mailed on Nov. 8, 2023, 9 pages.

International Search Report and Written Opinion received for PCT Application No. PCT/IB2023/057667, mailed on Nov. 28, 2023, 12 pages.

International Search Report and Written Opinion received for PCT Application No. PCT/IB2023/057668, mailed on Nov. 27, 2023, 15 pages.

International Search Report and Written Opinion received for PCT Application No. PCT/IB2023/057673, mailed on Apr. 29, 2024, 9 pages.

International Search Report and Written Opinion received for PCT Application No. PCT/IB2023/057675, mailed on Mar. 5, 2024, 15 pages.

International Search Report and Written Opinion received for PCT Application No. PCT/IB2023/057677, mailed on Nov. 30, 2023, 9 pages.

Joss Pepe Strache, "Studies on Enantioselective Nickel-Catalyzed Hydrocyanation and Chromane Natural Products", 2023, 295 pages.

Kee et al., A new class of chelating diphosphite: Synthesis and complexation of the silylated diphosphites [(R1O)2PO] 2SiR2R3 (R1 = Me, Et; R2 , R3 = Me, Ph, H, Ch CH2), Polyhedron, vol. 11, Issue 1, 1992, pp. 135-137.

Li et al., "Design and Synthesis of a Novel Triptycene-based Ligand for Modeling Carboxylate-Bridged Diiron Enzyme Active Sites", NIH Public Access, Org Lett., vol. 13, Issue 19, 2011, pp. 5052-5055.

Li et al., "Facile Synthesis of Enantiopure 1,1' -Spirobiindane-7,7' -diol and Its 4,4' -Derivatives: Application in Enantioselective Addition of Diethylzinc to Aromatic Aldehydes", Synthesis, No. 17, 2004, pp. 2805-2808.

Maji et al., "Cyclometalated complexes derived from calix[4]arene bisphosphites and their catalytic applications in cross-coupling reactions", Journal of Organometallic Chemistry, vol. 696, Issue 20, Oct. 1, 2011, pp. 3169-3179.

Maji et al., "Palladium and platinum complexes of chiral and achiral calix[4]arene bisphosphite ligands", Polyhedron, vol. 27, Issue 17, Nov. 25, 2008, pp. 3519-3527.

N. S. Imyanitov, "Cone angle of ligands—Group IV and V compounds", Koordinatsionnaya Khimiya, 1985, vol. 11, No. 9, 1 page (Abstract Only).

Paciello et al., "Chelated Bisphosphites with a Calix[4]arene Backbone: New Ligands for Rhodium-Catalyzed Low-Pressure Hydroformylation with Controlled Regioselectivity", vol. 38, Issue 13-14, pp. 1920-1923.

Panayiotis V. Ioannou, "Synthesis of arsinolipids: II. A non-isosteric analogue of fully acylated cardiolipin", Chemistry and Physics of Lipids, vol. 117, Issues 1-2, Aug. 2002, pp. 7-18.

Shahlai et al., "Synthesis of Supertriptycene and Two Related Iptycenes", The Journal of Organic Chemistry, vol. 56, Issue 24, 1991, pp. 6905-6912.

Smith et al., "Toward the Rhodium-Catalyzed Bis-Hydroformylation of 1,3-Butadiene to Adipic Aldehyde", Organometallics, vol. 30, 2011, pp. 3643-3651.

Sood et al., "Phosphorus-Based p-tert-Butylcalix[5]arene Ligands", Inorganic Chemistry, vol. 43, No. 9, 2004, pp. 2975-2980.

Steyer et al., "Bis-phosphites and bis-phosphinites based on distally-functionalised calix[4]arenes: coordination chemistry and use in rhodium-catalysed, low-pressure olefin hydroformylation", Dalton Transactions, 2005, pp. 1301-1309.

Sum et al., "Synthesis, characterization and reactivity of the silylated diphosphites [(R1O)2PO]2SIR2R3 (R1double bond Me, Et; R2, R3double bond Me, Ph, H, CHdouble bondCH2). Crystal structure of [MnBr(CO)32SiMe2]", Polyhedron, vol. 11, Issue 14, 1992, pp. 1743-1754.

Thiel et al., "A Simple Nickel Catalyst Enabling an E-Selective Alkyne Semihydrogenation", Chemistry—A European Journal, vol. 26, 2020, pp. 1597-1603.

Wassenaar et al., "INDOLPhosphole and INDOLPhos Palladium—Allyl Complexes in Asymmetric Allylic Alkylations", Organometallics, vol. 28, 2009, pp. 2724-2734.

Yu et al., "Enantioselective Nickel-Catalyzed Migratory Hydrocyanation of Nonconjugated Dienes", Angew. Chem Int Ed Engl., vol. 59, 2020, pp. 21436-21441.

(56) References Cited

OTHER PUBLICATIONS

Yu et al., "Highly Enantioselective Nickel-Catalyzed Hydrocyanation of Disubstituted Methylenecyclopropanes Enabled by TADDOL-basedDiphosphite Ligands", Organic Letters, vol. 22, Issue 2, 2020, pp. 594-597.
Yu et al.,"Regio-, Chemo-, and Enantioselective Ni-Catalyzed Hydrocyanation of 1,3-Dienes", Organic Letters, vol. 23, Issue 3, 2021, pp. 930-935.
Trishin et al., "Interaction of Aryldichlorophosphines and Aryldichlorophosphites with Primary Aromatic Amines", Journal of General Chemistry, vol. 49, 1979, 14 pages (Including English Translation).
Chesterton et al., "Making the Baskets: Synthesis of Calixarenes", Chapter 2, Apr. 23, 2025, pp. 10-31.
Bagher, et al., "Introduction to Radio Active Materials", International Journal of Renewable and Sustainable Energy, vol. 3, No. 3, 2014, pp. 59-67.
Baker, et al., "Chelating Diphosphite Complexes of Nickel(0) and Platinum(0): their Remarkable Stability and Hydrocyanation Activity", Journal of the Chemical Society, Chemical Communications, 1991, pp. 803-804.
Baker, et al., "Chiral aryl diphosphites: a new class of ligands for hydrocyanation catalysis", Journal of the Chemical Society, Chemical Communications, 1991, pp. 1292-1293.
Green, M.L.H., "A New Approach to the Formal Classification of Covalent Compounds of the Elements", Journal of Organometallic Chemistry, vol. 500, 1995, pp. 127-148.
Greenwood, et al., "Chemistry of Elements", School of chemistry, Chapters 20-25, 1997, pp. 944-1112.
Kruger, et al., "Synthesis and Molecular Structure of Chiral Bis(1,3,2-dioxaphospholanes)", Zeitschrift fuer Anorganische and Allgemeine Chemie, 2000, 626(10), pp. 2228-2234.
Patil, et al., " Exploration and Investigation of Periodic Elements for Electrocatalytic Nitrogen Reduction", Department of Chemistry, 2020, 44 Pages.
Plant, et al., "Radioactivity and Radioelements", In Journal of Pollutants, Human Health and the Environment: A Risk Based Approach, 2011, pp. 115-146.
Zhang, et al., "Recent progress in transition-metal-catalyzed hydrocyanation of nonpolar alkenes and alkynes", Organic & Biomolecular Chemistry, 2020, pp. 391-399.

* cited by examiner

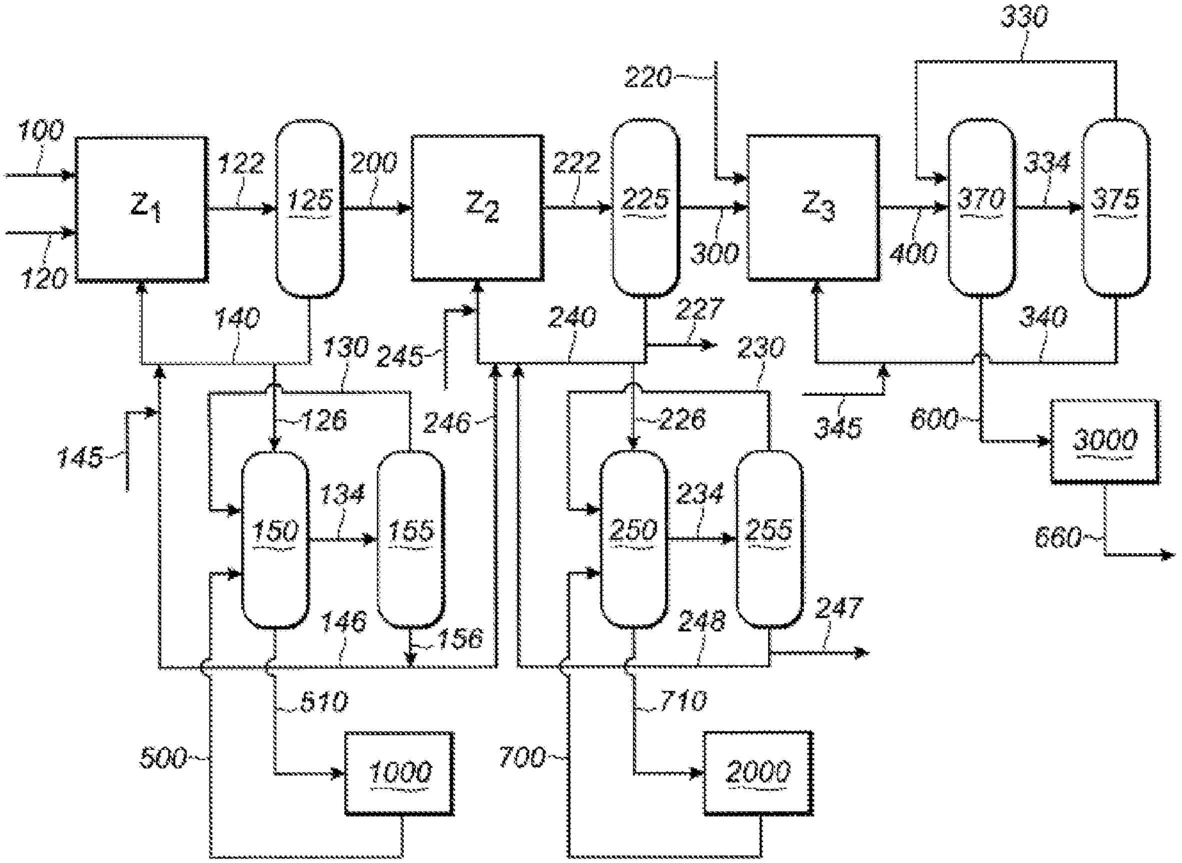
100
120
$Z_1$
122
125
200
$Z_2$
222
225
300
$Z_3$
220
400
370
334
375
330
340
600
3000
660
345
140
130
126
145
150
134
155
146
156
246
245
240
227
230
226
250
234
255
248
247
510
1000
500
710
2000
700

BIDENTATE PHOSPHITE LIGANDS, CATALYTIC COMPOSITIONS CONTAINING SUCH LIGANDS, AND CATALYTIC PROCESSES UTILIZING SUCH CATALYTIC COMPOSITIONS

REFERENCE TO RELATED APPLICATIONS

This application claims the benefit of U.S. Provisional Application No. 63/394,315 filed 2 Aug. 2022 and GB Application No. 2215077.5 filed 13 Oct. 2022. The entire contents of these applications are incorporated herein by reference in their entirety.

FIELD

The present application relates to a bidentate phosphite ligands, catalytic compositions containing such ligands, and catalytic processes utilizing such catalytic compositions.

BACKGROUND

Phosphorus ligands are ubiquitous in catalysis and are used for a number of commercially important chemical transformations. Phosphorus ligands commonly encountered in catalysis include phosphines (A), and phosphites (B), shown below. In these representations, R can be virtually any organic group. Monophosphine and monophosphite ligands are compounds which contain a single phosphorus atom which serves as a donor to a metal. Bisphosphine, bisphosphite, and bis(phosphorus) ligands in general, contain two phosphorus donor atoms and normally form cyclic chelate structures with transition metals.

A

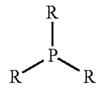

B

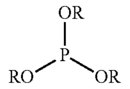

There are several industrially important catalytic processes employing phosphorus ligands. For example, U.S. Pat. No. 5,910,600 to Urata, et al. discloses that bisphosphite compounds can be used as a constituting element of a homogeneous metal catalyst for various reactions such as hydrogenation, hydroformylation, hydrocyanation, hydrocarboxylation, hydroamidation, hydroesterification and aldol condensation.

Some of these catalytic processes are used in the commercial production of polymers, solvents, plasticizers and other commodity chemicals. For example, hydrocyanation of 1,3-butadiene and/or 3-pentenenitrile is a well-known route to the production of adiponitrile, a precursor in the manufacture of nylon-6,6. Consequently, due to the extremely large worldwide chemical commodity market, even small incremental advances in yield or selectivity in any of these commercially important reactions are highly desirable. Furthermore, the discovery of certain ligands that may be useful for applications across a range of these commercially important reactions is also highly desirable not only for the commercial benefit, but also to enable consolidation and focusing of research and development efforts to a particular group of compounds.

U.S. Pat. No. 5,512,696 to Kreutzer, et al. discloses a hydrocyanation process using a multidentate phosphite ligand, and the patents and publications referenced therein describe hydrocyanation catalyst systems pertaining to the hydrocyanation of ethylenically unsaturated compounds. U.S. Pat. Nos. 5,723,641, 5,663,369, 5,688,986 and 5,847,191 disclose processes and catalyst compositions for the hydrocyanation of mono-ethylenically unsaturated compounds using zero-valent nickel and multidentate phosphite ligands, and Lewis acid promoters.

U.S. Pat. No. 5,821,378 to Foo, et al. discloses a liquid phase process for the hydrocyanation of diolefinic compounds to produce nonconjugated acyclic nitriles as well as a liquid phase process for the isomerization of those nitriles to 3- and/or 4-monoalkene linear nitriles where the reactions are carried out in the presence of zero-valent nickel and a multidentate phosphite ligand. Other catalytic processes for the hydrocyanation of olefins and the isomerization of monoalkene nitriles are described in the patents and publications referenced therein. Published International Application WO99/06357 discloses multidentate phosphite ligands having alkyl ether substituents on the carbon attached to the ortho position of the terminal phenol group for use in a liquid phase process for the hydrocyanation of diolefinic compounds to produce nonconjugated acyclic nitriles as well as a liquid phase process for the isomerization of those nitriles to 3- and/or 4monoalkene linear nitriles.

While the catalyst systems described above may represent commercially viable catalysts, it always remains desirable to provide even more effective, higher performing catalyst precursor compositions, catalytic compositions and catalytic processes to achieve full commercial potential for a desired reaction. The effectiveness and/or performance may be achieved in any or all of rapidity, selectivity, efficiency or stability, depending on the reaction performed. It is also desirable to provide such improved catalyst systems and/or processes which may be optimized for one or more commercially important reactions such as hydroformylation, hydrocyanation or isomerization.

SUMMARY

In one aspect, the present application provides a bidentate phosphite ligand comprising a backbone having a structure of acenaphthene-1,2-diol in which the hydrogen atoms of the hydroxyl groups have each been replaced by a $P(OR^1)_2$ group, where $R^1$ is an aryl radical.

In another aspect, the present application provides a bidentate phosphite ligand having the following structure:

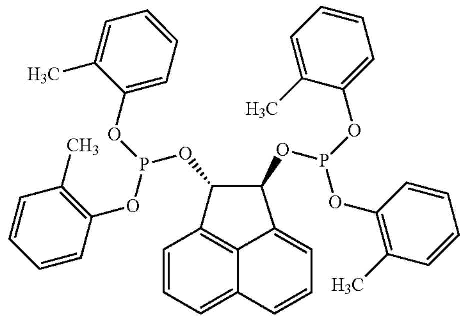

In a further aspect, the present application provides a catalyst complex comprising a multidentate phosphite ligand as described herein and at least one transition metal.

In yet a further aspect, the present application provides a process for the hydrocyanation of an organic compound containing at least one olefinic group comprising reacting the organic compound with hydrogen cyanide in the presence of a catalyst complex as described herein.

In still a further aspect, the present application provides a process for the isomerization of a monoethylenically unsaturated compound wherein said compound is contacted with a catalyst complex as described herein.

BRIEF DESCRIPTION OF THE DRAWINGS

FIG. 1 is a simplified block diagram of an integrated process according to one example of present disclosure for manufacturing adiponitrile comprising the steps of hydrocyanating 1,3-butadiene, isomerizing 2-methyl-3-butenenitrile and hydrocyanating 3-pentenenitrile.

DETAILED DESCRIPTION OF THE EMBODIMENTS

Described herein is a novel bidentate phosphite ligand and a catalyst complex comprising the bidentate phosphite ligand and at least one transition metal. Also described are catalytic processes using the catalyst complex, such as the hydrocyanation of organic compounds containing at least one olefinic group, particularly 1,3-butadiene and 3-pentenenitrile, and the double bond isomerization of monoethylenically unsaturated compounds, such as 2-methyl-3-butenenitrile.

Bidentate Phosphite Ligand

In its broadest aspect, the novel bidentate phosphite ligand comprises a backbone having a structure of acenaphthene-1,2-diol in which the hydrogen atoms of the hydroxyl groups have each been replaced by a $P(OR^1)_2$ group, where $R^1$ is an aryl radical. As used herein, the term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. In one embodiment, each aryl radical $R^1$ is a benzyl radical.

A non-limiting example of a suitable bidentate phosphite ligand includes:

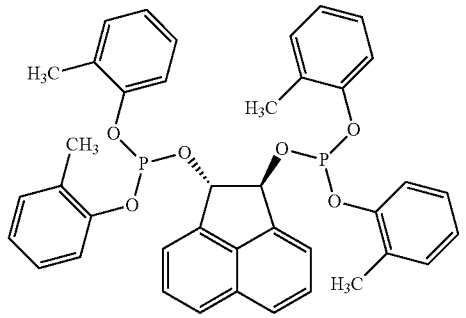 [SMILES: Cc1ccccc1OP(Oc1ccccc1C)O[C@H]1c2cccc3cccc(c23)[C@@H]1OP(Oc1ccccc1C)Oc1ccccc1C]

Ligand A

Synthesis of Bidentate Phosphite Ligand

The novel bidentate phosphite ligand described herein may be produced by reacting acenaphthene-1,2-diol with a phosphorochloridite of the formula $(R^1O)_2PCl$:

The method used to produce the phosphorochloridite is not critical since a number of available methods are known in the art. For example, each may be synthesized by the reaction of $PCl_3$ with an aryl alcohol or diol in the presence of a suitable organic base to first prepare a phosphorodichloridite, followed, where necessary, by further reaction with the aryl alcohol to prepare the desired phosphorochloridite. Selective syntheses for suitable phosphorchloridites are disclosed, for example, in PCT Publication WO 2004/050588 and EP 2,243,763 B1.

The resulting phosphorchloridite is then contacted with acenaphthene-1,2-diol and a base, preferably a tertiary organic amine comprising a basic nitrogen atom or a plurality of basic nitrogen atoms, under conditions to promote reaction between the phosphorchloridite and the precursor to produce the desired ligand. The contacting is conveniently effected by at least one contacting method selected from the group consisting of (i) feeding the diol to a mixture of phosphorchloridite and tertiary organic amine, and (ii) feeding the diol and the tertiary organic amine either separately or as a mixture to the phosphorochloridite. In embodiments, the feeding is controlled such that the ratio of the number of moles of phosphorchloridite in the reaction mixture divided by the number of moles of diol fed to the reaction mixture is at least 2.0, such as from 2.1 to 2.7, during all stages of the contacting, while the ratio of the number of moles of basic nitrogen atoms from the tertiary organic amine fed to the reaction mixture divided by the number of moles of phosphorchloridite in the reaction mixture is at least 1.0, such as from 1.0 to 1.5, during all stages of the contacting. Generally, the contacting occurs at a temperature from about 10° C. to about 110° C., such as from about 20° C. to about 110° C., such as from about 30° C. to about 110° C., such as from about 40° C. to about 110° C., such as from about 50° C. to about 110° C., such as from about 60° C. to about 110° C.

Examples of suitable tertiary organic amines comprising a single basic nitrogen atom may be a (R') (R") (R") N compound wherein R', R", and R' are independently selected from the group consisting of $C_1$ to $C_{10}$ alkyl and $C_6$ to $C_{10}$ aryl radicals, or may be a tertiary aromatic amine compound, for example pyridine, or may be a combination of tertiary organic amines comprising a single basic nitrogen atom. One example of a suitable amine includes a trialkylamine with the alkyl group individually selected and having 1 to 10 carbon atoms, such as triethylamine. Other examples include tertiary organic amines including a plurality of basic nitrogen atoms have nitrogen atoms with no N—H bonds; for example N,N,N',N'-tetramethylethylenediamine.

In some embodiments, the reaction mixture can include at least one hydrocarbon solvent. For example, the backbone precursor can be fed to a reaction zone containing the phosphorchloridite as a solution of the precursor in a hydrocarbon solvent. In some examples, the hydrocarbon solvent can be selected from the group consisting of linear acyclic $C_5$ to $C_{18}$ aliphatic hydrocarbons, branched acyclic $C_5$ to $C_{18}$ aliphatic, unsubstituted cyclic $C_5$ to $C_{18}$ aliphatic, substituted cyclic $C_5$ to $C_{18}$ aliphatic, unsubstituted $C_6$ to $C_{10}$ aromatic, and $C_7$ to $C_{18}$ substituted aromatic hydrocarbons. The hydrocarbon solvent can be selected from the group consisting of hydrocarbons whose boiling point is from 70° C. to 145° C. at atmospheric pressure. Examples of suitable aromatic hydrocarbon solvents include $C_{1-5}$-substituted benzenes, such as xylenes and toluene.

Contacting methods (i) and (ii) may be performed in semi-batch, continuous flow, or a combination of semi-batch and continuous flow modes. For example, the diol can be fed continuously or discontinuously to a stirred vessel comprising the phosphorchloridite and tertiary organic amine. In addition, the diol can be fed continuously or discontinuously to a tubular reactor comprising a continuous flow of a mixture of the phosphorchloridite and tertiary organic amine.

More details of suitable methods of producing the ligands described herein can be found in U.S. Pat. No. 9,221,852 B2, the entire contents of which are incorporated herein by reference.

Using the process described above, ligand A can be produced by reacting acenaphthene-1,2-diol with a phosphorochloridite produced by reacting $PCl_3$ with ortho-cresol.

Catalyst Complex

The bidentate phosphite ligand disclosed herein is useful in combination with a transition metal to form a catalyst complex (a chelate). The catalyst complex is useful for olefin hydrocyanation, for example, hydrocyanation of diolefins, such as 1,3-butadiene. Particularly for hydrocyanation of a monoolefin, such as 3-pentenenitrile, a catalyst promoter such as a Lewis acid may optionally be used. The catalyst complex is also useful in double bond isomerization of a monoethylenically unsaturated compound, such as 2-methyl-3-butenenitrile.

The transition metal employed in the catalyst complex may be any transition metal capable of carrying out the desired catalytic transformations and may additionally contain labile ligands which are either displaced during the catalytic reaction or take an active part in the catalytic transformation. Any of the transition metals may be considered in this regard. The preferred metals are those comprising group VIII of the Periodic Table. The preferred metals for hydrocyanation and/or isomerization are nickel, cobalt, and palladium, with nickel being especially preferred.

Nickel compounds can be prepared or generated according to techniques well known in the art, as described, for example, in U.S. Pat. Nos. 3,496,217; 3,631,191; 3,846,461; 3,847,959; and 3,903,120, which are incorporated herein by reference. Zero-valent nickel complexes that contain ligands which can be displaced by the organophosphorus ligand may be used as a source of nickel. Two such zero-valent nickel complexes are $Ni(COD)_2$ (COD is 1,5-cyclooctadiene) and $Ni\{P(O\text{-}o\text{-}C_6H_4CH_3)_3\}_2(C_2H_4)$, both of which are known in the art. Alternatively, divalent nickel compounds may be combined with a reducing agent, to serve as a source of nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$.

One method of preparing zero-valent nickel with high activity for complexation with phosphorus-containing ligands is described U.S. Pat. No. 10,537,885 and comprises calcining first nickel(II)-containing particles in an atmosphere comprising oxidizing constituents and typically at a temperature 350° C. to 600° C. for a time sufficient to remove volatile components from the first nickel(II)-containing particles and generate second nickel(II)-containing particles. The second nickel(II)-containing particles are then heated in a reducing atmosphere while rotating or turning the second nickel(II)-containing particles in a rotary processor at 275° C. to 360° C. for a time sufficient to generate a free-flowing particulate nickel metal (Ni(0)) product, wherein the reducing atmosphere is free of added water or steam not produced by the reducing, and wherein a $H_2$/Ni molar ratio is employed during the reducing step of between about 1.9 and 2.5.

Elemental nickel, preferably nickel powder, when combined with a halogenated catalyst, as described in U.S. Pat. No. 3,903,120, is also a suitable source of zero-valent nickel.

In some embodiments, elemental nickel may be employed in particulate form having a BET Specific Surface Area (SSA) of at least about 1 $m^2$/gm and an average crystallite size less than about 100 nm. The nickel particulate form can have at least 10% of the crystallites in the nickel form with a diameter (C10) of less than about 10 nm, and/or there are on average at least about 1015 surface crystallites per gram nickel. A ratio of BET SSA to C50 for the nickel particulate form can be at least about $0.1\times10^9$ m/gm and preferably at least about $0.4\times10^9$ m/gm. Examples of such small particle forms of nickel and methods of their preparation can be found in U.S. Pat. No. 9,050,591, the entire contents of which are incorporated herein by reference.

Depending upon the desired reaction to be performed, the catalyst composition may also include one or more Lewis acid promoters, which affect both the activity and the selectivity of the catalyst system. The promoter maybe an inorganic or organometallic compound in which the at least one of the elements of said inorganic or organometallic compound is selected from scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, CuCl, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(iso\text{-}C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$. Suitable promoters are further described in U.S. Pat. Nos. 3,496,217; 3,496,218; and 4,774,353. These include metal salts (such as $ZnCl_2$, $CoI_2$, and $SnCl_2$), and organometallic compounds (such as $RAlCl_2$, $R_3SnO_3SCF_3$, and $R_3B$, where R is an alkyl or aryl group). U.S. Pat. No. 4,874,884 describes how synergistic combinations of promoters can be chosen to increase the catalytic activity of the catalyst system. Preferred promoters include $CdCl_2$, $FeCl_2$, $ZnCl_2$, $B(C_6H_5)_3$, and $(C_6H_5)_3SnX$, where X is $CF_3SO_3$, $CH_3C_6H_5SO_3$, or $(C_6H_5)_3BCN$. The mole ratio of promoter to nickel present in the reaction can be within the range of about 1:16 to about 50:1.

Catalytic Processes Employing the Catalyst Complex

The catalyst complex described above is useful in a wide variety of catalytic reactions such as hydrogenation, hydroformylation, hydrocyanation, hydrocarboxylation, hydroamidation, hydroesterification, aldol condensation and double bond isomerization of monoethylenically unsaturated compounds. Preferred reactions include hydroformylation, in which an olefin is reacted with carbon monoxide and hydrogen to produce an aldehyde, and especially hydrocyanation, in which an olefin is reacted with hydrogen cyanide to produce a nitrile. A particularly preferred use of the catalyst complex described above, in which the transition metal is nickel, is in the catalytic hydrocyanation of 1,3-butadiene to produce 3-pentenenitrile and then to convert the 3-pentenenitrile to adiponitrile. In embodiments, in a first reaction zone, 1,3-butadiene is reacted with hydrogen cyanide in the presence of a first catalyst to produce pentenenitriles comprising 3-pentenenitrile and 2-methyl-3-butenenitrile. In an optional second reaction zone, 2-methyl-3-butenenitrile, recovered from the first reaction zone, is isomerized to 3-pentenenitrile over a second catalyst. In a third reaction zone, 3-pentenenitrile recovered from the first and second reaction zones is reacted with hydrogen cyanide in the presence of a third catalyst and a Lewis acid to produce adiponitrile. One, two or all of the first, second and third catalysts can be the catalyst complex described above.

For example, 3-pentenenitrile (3PN) may be formed from 1,3-butadiene through a series of reactions as illustrated in equations 1 and 2 below.

$$CH_2{=}CHCH{=}CH_2 + HC{\equiv}N \longrightarrow \quad (1)$$

BD $$CH_3CH{=}CHCH_2C{\equiv}N + CH_2{=}CHCH(CH_3)C{\equiv}N$$

3PN 2M3BN $$CH_2{=}CHCH(CH_3)C{\equiv}N \rightleftharpoons CH_3CH{=}CHCH_2C{\equiv}N + \quad (2)$$

2M3BN 3PN $$CH_2{=}CHCH_2CH_2C{\equiv}N + CH_3CH_2CH{=}CHC{\equiv}N +$$

4PN 2PN $$CH_3CH{=}C(CH_3)C{\equiv}N$$

2M2BN

According to abbreviations used herein, BD is 1,3-butadiene, 2PN is 2-pentenenitrile, 3PN is 3-pentenenitrile, 4PN is 4-pentenenitrile, 2M2BN is 2-methyl-2-butenenitrile, 2M3BN is 2-methyl-3-butenenitrile. MGN is 2-methylglutaronitrile and ADN is adiponitrile.

In the presence of transition metal complexes comprising various phosphorus-containing ligands, such as the catalyst complex described herein, dinitriles such as ADN, MGN, and ethylsuccinonitrile (ESN) may be formed by the hydrocyanation of 3PN and 2M3BN, as illustrated in Equations 3 and 4 below. Equation 4 also shows that 2M2BN can be formed when 2M3BN undesirably isomerizes in the presence of a Lewis acid promoter that may be carried over from a pentenenitrile hydrocyanation reaction zone.

$$CH_3CH{=}CHCH_2C{\equiv}N + HC{\equiv}N \longrightarrow \quad (3)$$

3PN $$N{\equiv}CCH_2CH_2CH_2CH_2C{\equiv}N + N{\equiv}CCH_2CH_2CH(CH_3)C{\equiv}N +$$

ADN MGN $$N{\equiv}CCH_2CH(CH_2CH_3)C{\equiv}N + CH_2{=}CHCH_2CH_2C{\equiv}N +$$

ESN 4PN $$CH_3CH_2CH{=}CHC{\equiv}N + CH_3CH_2CH_2CH_2C{\equiv}N$$

2PN VN $$CH_2{=}CHCH(CH_3)C{\equiv}N + HC{\equiv}N \longrightarrow \quad (4)$$

2M3BN $$N{\equiv}CCH_2CH_2CH(CH_3)C{\equiv}N + CH_3CH{=}C(CH_3)C{\equiv}N$$

MGN 2M2BN

According to one aspect of the present disclosure, 3-pentenenitrile is made in a process comprising two steps. In the first step, 1,3-butadiene is reacted with hydrogen cyanide in a first reaction zone in the presence of a first catalyst complex comprising a transition metal, such as zero-valent nickel, and a first phosphorus-containing ligand to produce a reactor effluent comprising 3-pentenenitrile (3PN) and 2-methyl-3-butenenitrile (2M3BN). In the second step, at least a portion of the 2M3BN made in the first step is isomerized in a second reaction zone in the presence of a second catalyst complex comprising a transition metal, such as zero-valent nickel, and a second phosphorus-containing ligand to produce a reaction product comprising 3PN. The first catalyst complex may be the same or different from the second catalyst complex and may be a catalyst complex as described herein. Generally, the reactions in the first and second reaction zones are conducted in the absence of Lewis acid promoter.

An effluent stream comprising 3PN may be recovered from the second reaction zone. In addition, 3PN is generally also recovered, such as by distillation, from the reaction product of the first reaction zone. The recovered 3PN may be contacted with HCN in a third reaction step in a third reaction zone in the presence of a third catalyst complex comprising a transition metal, such as zero-valent nickel, and a third phosphorus-containing ligand. The third catalyst complex may be the same or different from the first and/or the second catalyst complex and may be a catalyst complex as described herein. The reaction in the third reaction zone takes place in the presence of Lewis acid promoter.

In addition to 3-pentenenitrile (3PN) and 2-methyl-3-butenenitrile (2M3BN), the reaction product from the first reaction zone further comprises dinitriles. These dinitriles comprise adiponitrile (ADN), which may be formed by the reaction of 3-pentenenitrile (3PN) with HCN and methylglutaronitrile (MGN), which may be formed by the reaction of 2-methyl-3-butenenitrile (2M3BN) with HCN. The formation of MGN in the first reaction zone is deleterious in that 2M3BN is converted before it can be recovered and isomerized into 3PN. In a process where 3PN is recovered and reacted with HCN to form ADN, the production of one mole of MGN in the first reaction zone results in a loss of two moles of HCN and one mole of BD, which could otherwise be converted to ADN. Accordingly, unwanted production of MGN in the first reaction zone results in unwanted reduction of ADN yield, based on moles of HCN and BD reacted.

Conversion of 1,3-Butadiene to 3-Pentenenitrile

The 1,3-butadiene feedstock to the first reaction zone may comprise at least 98 wt % 1,3-butadiene based on the total weight of the feedstock, preferably at least 99 wt %, and more preferably at least 99.5 wt %. In one embodiment, the feedstock comprises from 99.5 to 99.9 wt % 1,3-butadiene based on the total weight of the feedstock. The balance of the feedstock may comprise residual levels of impurities generally found in commercial BD feedstocks, such as butane, butenes, 1,2-butadiene and acetylenes such as propyne. Generally, the BD-containing feed comprises less than a total of 100 ppm acetylenes. The BD feedstock may also comprise tertiary-butylcatechol (TBC), for example, 4-tert-butylcatechol. A portion of TBC present in the feedstock may optionally be removed before charging the 1,3-butadiene to the first reaction step.

The HCN feed to the first reaction zone and the third reaction zone may be a product of the Andrussow process that is dried to less than about 250 ppm water, for example, less than 125 ppm water, for example, less than 80 ppm water, by distillation prior to entry into olefin hydrocyanation reaction zones. However, the HCN feed will usually contain at least some water. Very dry HCN is unstable and, for this reason, it may be undesirable to provide completely anhydrous HCN. Accordingly, the HCN feed may comprise at least 10 ppm, for example, at least 25 ppm, for example, at least 50 ppm, water. The HCN feed is preferably substantially free of carbon monoxide, oxygen and ammonia. This HCN can be introduced to the first reaction zone and the third reaction zone as a vapor, liquid, or mixtures thereof; see, for example, European Patent Publication No. 1 344 770. As an alternative, a cyanohydrin can be used as the source of HCN; see, for example, U.S. Pat. No. 3,655,723.

The overall feed molar ratio of the BD to HCN to the first reaction zone may be in the range of about 1:1 to about 100:1, for example, in the range of about 1:1 to about 2:1. Excess BD within the first reaction zone may decrease the formation of dinitriles during the BD hydrocyanation reaction. The feed molar ratio of HCN to catalyst to the first reaction zone of may be in the range of about 5:1 to about 100,000:1, for example, in the range about 100:1 to about 5,000:1.

The reaction conditions employed in the first reaction zone may comprise a temperature within the range of about −25° C. to about 200° C., for example, within the range of about 0° C. to about 150° C. Generally, the reaction pressure should be sufficient to maintain the BD and HCN in contact with the catalyst dissolved in the liquid reaction mixture, with such pressure at least, in part, being a function of the amount of unreacted BD present in the reaction mixture. Though the disclosed process is not limited by an upper limit of pressure for the first reaction step, for practical purposes the pressure may generally range from about 15 psia to about 300 psia (about 1.03 bar to about 20.7 bar).

A non-oxidizing and anhydrous environment retards oxidative deactivation of the catalyst during the first reaction step. Accordingly, a dry inert atmosphere, e.g., nitrogen, is normally used in the first reaction zone, although air may be used at the expense of loss of a portion of the catalyst through oxidation and hydrolysis.

In the first reaction step, the HCN feed, the BD-containing feed, and the catalyst composition may be contacted in any suitable reactor or reactors known to one skilled in the art. Examples include continuous stirred-tank reactors, loop-type bubble column reactors, gas circulation reactors, bubble column reactors, tubular reactors, or combinations thereof, optionally with apparatus for removing at least a portion of the heat of reaction.

The residence time in the first reaction zone is typically determined by the desire to obtain a certain degree of conversion of BD, HCN, or a combination thereof. Generally, residence times will be in the range of about 0.1 hour to about 15 hours, for example, in the range of about 1 hour to about 10 hours. The HCN conversion may be, for example, greater than 99%. Generally, BD conversion in the first reaction zone may be less than 99%, for example, between 80 and 95% overall, for example 90% overall. Staged HCN addition within the first reaction zone may be used.

Separation of the Products of First Reaction Zone

The reaction of 1,3-butadiene and HCN in the presence of the first catalyst in the first reaction zone produces a first reaction effluent comprising 3-pentenenitrile, 2-methyl-3-butenenitrile, unreacted 1,3-butadiene and the first catalyst. These components of the reaction effluent may be separated, at least partially, by one or more distillation steps. In particular, these distillation steps may take place in one or more distillation columns, to provide: 1) at least one 1,3-butadiene-enriched stream; 2) a 2-methyl-3-butenenitrile-enriched stream; 3) a 3-pentenenitrile-enriched stream; and 4) a first catalyst-enriched stream. These streams are enriched with a particular component in that they have greater concentrations of these components than the effluent from the first reaction zone. In embodiments, the 2-methyl-3-butenenitrile-enriched stream and 3-pentenenitrile-enriched stream may each contain less than a total of 500 parts per million by weight of phosphorus-containing ligand, for example, less than 350 parts per million by weight of phosphorus-containing ligand, for example, less than 200 parts per million by weight of phosphorus-containing ligand.

In embodiments, at least partial separation of the 3-pentenenitrile and the 2-methyl-3-butenenitrile in the reaction effluent from the first reaction zone may be achieved by a multi-stage distillation process. For example, such a process may include a first distillation column apparatus comprising a feed inlet; an upper draw outlet; and a bottom draw outlet. The reaction effluent comprising 3PN, 2M3BN, and at least one catalyst including a phosphorus-containing ligand, may be supplied to a feed stage of the first distillation column through the feed inlet. The distillation column may include a stripping section, a rectifying section or both. There may be at least one stage of separation between the feed inlet and the upper draw outlet. A pentenenitrile-enriched stream comprising 3-pentenenitrile and 2-methyl-3-butenenitrile may be withdrawn from the upper draw outlet. This stream is depleted of the at least one phosphorus-containing ligand, relative to the phosphorus-containing ligand stream fed to the distillation column. A pentenenitrile-depleted stream may be withdrawn from the bottom draw outlet. This pentenenitrile-depleted stream is enriched with the phosphorus-containing ligand, relative to the phosphorus-containing ligand stream fed to the distillation column. The first distillation column may be operated such that the pentenenitrile-depleted stream comprises at least 5% by weight of pentenenitrile including the sum of 3-pentenenitrile and 2-methyl-3-butenenitrile.

The pentenenitrile-enriched stream comprising 3-pentenenitrile and 2-methyl-3-butenenitrile may be distilled in a second distillation column to obtain a 2-methyl-3-butenenitrile-enriched stream as a top product and a 2-methyl-3-butenenitrile-depleted stream (i.e. a 3-pentenenitrile-enriched stream) as a bottom product. The bottom stream enriched in 3-pentenenitrile may be recycled to the first reaction zone, whereas the top product enriched in 2-methyl-3-butenenitrile may be fed to the second reaction zone for isomerization to produce additional 3-pentenenitrile.

The first catalyst-enriched stream separated from the first reaction zone effluent is at least partially recycled to the first reaction zone and in some cases the second reaction zone. However, since this stream contains catalyst degradation products and reaction byproducts and may be depleted in nickel, a portion of the first catalyst enriched stream is generally withdrawn and fed to a first catalyst purification system. In embodiments, at least 80%, preferably at least 90%, for example, 93 to 96%, at least 99%, at least 99.9%, and substantially all of the first catalyst is recycled, with the remainder being fed to the purification system. Typically, the purification system comprises one or more liquid/liquid extraction zones, where the first catalyst-enriched stream is contacted with a non-polar solvent, such as cyclohexane or other cyclic or linear alkane, and a polar solvent, such as adiponitrile, which is immiscible with the non-polar solvent, preferably in counter current flow. Typically, the temperature in the extraction zone(s) to facilitate phase separation and catalyst extraction may be from 25° C. to 135° C., for example, 25° C. to 90° C., for example, 50° C. to 75° C. In the extraction zone(s), there is formed a non-polar phase comprising the non-polar solvent and the first catalyst and a polar phase (e.g., a raffinate) comprising the polar solvent and, for example, the reaction byproducts and catalyst degradation products.

The non-polar phase is recovered from the extraction zone(s) and then fed to a separation system, conveniently one or more distillation columns, where the purified first catalyst is separated from the non-polar solvent and then returned to either the first or second reaction zone, optionally after the addition of further nickel to the catalyst. The non-polar solvent can then be recycled to the liquid/liquid extraction zones. Similarly, the raffinate phase is separately recovered from the extraction zone(s) and then fed to a further separation system, conveniently one or more distillation columns, where the reaction byproducts and catalyst degradation products are separated from the polar solvent for further treatment and/or disposal. The polar solvent can then be recycled to the liquid/liquid extraction zones.

Isomerization of 2-Methyl-3-Butenenitrile

The 2-methyl-3-butenenitrile (2M3BN)-enriched stream separated from the first reaction zone effluent is fed to the second reaction zone, where the 2M3BN is isomerized in the presence of a second catalyst complex to produce a reaction product comprising 3PN. Typically, the feed to the second reaction zone comprises at least 30 wt % 2M3BN and less than 70 wt % of pentenenitriles other than 2M3BN. The second catalyst complex generally comprises a transition metal, such as zero-valent nickel, and a ligand and may be the same or different from the first catalyst complex. If a monodentate phosphorus-containing ligand is used for the second catalyst complex, the molar ratio of monodentate ligand to zero valent nickel in the catalyst for the isomerization reaction may be from about 1:1 to about 50:1, for example, from about 1:1 to about 30:1. When a bidentate ligand is used, the molar ratio of bidentate ligand to zero valent nickel in the catalyst for the isomerization reaction may be from 1:1 to 10:1, for example, from 1:1 to 5:1.

To facilitate the isomerization of 2M3BN to produce 3PN, the reaction temperature in the second reaction zone may be maintained within the range of about 0° C. to about 200° C., for example, within the range of about 50° C. to about 165° C., while the pressure generally ranges from about 15 psia to about 300 psia (about 1.03 bar to about 20.7 bar). The feed molar ratio of 2M3BN to catalyst for the isomerization reaction step is generally greater than 1:1, usually in the range from about 5:1 to 20,000:1, for example, from about 100:1 to about 5,000:1. Suitable reactors for the isomerization reaction include continuous stirred-tank reactors, loop-type bubble column reactors, gas circulation reactors, bubble column reactors, tubular reactors, or combinations thereof, optionally with apparatus for removing at least a portion of the heat of reaction. The residence time in the second reaction zone for the isomerization reaction may be from about 0.1 hour to about 15 hours, for example, from about 1 hour to about 10 hours.

Separation of the Products of the Second Reaction Zone

The effluent from the second reaction zone mainly comprises 3-pentenenitrile, residual 2-methyl-3-butenenitrile and the second catalyst. These components may be separated, at least partially by one or more distillation steps, to provide: 1) a second 2-methyl-3-butenenitrile-enriched stream; 2) a second 3-pentenenitrile-enriched stream; and 3) a second catalyst-enriched stream. The second 2-methyl-3-butenenitrile-enriched stream and the second 3-pentenenitrile-enriched stream may each contain less than a total of 500 parts per million by weight of the phosphorus-containing ligand. For example, the second 3-pentenenitrile-enriched stream may contain less than 300 ppm, for example, less than 100 ppm, of the phosphorus-containing ligand.

The second 3-pentenenitrile-enriched stream may comprise small amounts of 2-methyl-3-butenenitrile, which may be separated from 3-pentenenitrile in one or more distillations columns, where 2-methyl-3-butenenitrile is recovered as a top product and 3-pentenenitrile is recovered as a bottom product. For example, the first and second 3-pentenenitrile-enriched streams may be combined and distilled in a single or shared distillation column or these streams may be distilled in separate distillation columns. 2-methyl-3-butenenitrile recovered from such distillation may be passed as feed to the second reaction zone, and 3-pentenenitrile recovered from such distillation may be passed as feed to the third reaction zone.

The second 3-pentenenitrile-enriched stream may further comprise (Z)-2-methyl-2-butenenitrile and may be distilled to obtain a (Z)-2-methyl-3-butenenitrile-enriched stream, comprising 2-methyl-3-butenenitrile and (Z)-2-methyl-2-butenenitrile, along with other low boilers, as a top product, and a (Z)-2-methyl-2-butenenitrile-depleted stream, comprising 3-pentenenitrile, 2-methyl-3-butenenitrile, and, depending on distillation conditions, some (Z)-2-methyl-2-butenenitrile, as a bottom product. The 3-pentenenitrile and 2-methyl-3-butenenitrile may be separately recovered from the (Z)-2-methyl-2-butenenitrile-depleted stream for passage to the third reaction zone and recycle to the second reaction zone, respectively.

At least a portion of the second 3-pentenenitrile-enriched stream may be used to prepare a catalyst solution. In particular, at least a portion of the second 3-pentenenitrile-enriched stream may be passed into a catalyst reaction zone, wherein nickel metal reacts with the phosphorus-containing ligand to produce a catalyst solution, comprising catalyst and pentenenitriles. A portion of this catalyst solution may be passed into the second reaction zone. When the first and second catalysts comprise the same phosphorus-containing ligand, a portion of the catalyst may be passed to the first reaction zone.

The second catalyst-enriched stream recovered from the reaction effluent from the second reaction zone may be purified by liquid/liquid extraction as discussed above for the first catalyst-enriched stream separated from the first reaction zone effluent. In fact, where the first and second catalyst complexes are the same, a single liquid/liquid extraction system can be used to purify both catalysts.

Hydrocyanation of 3-Pentenenitrile to Adiponitrile

The 3-pentenenitrile produced in the first and second reaction zones is passed to a third reaction zone, where the 3PN is reacted with additional hydrogen cyanide in the presence of a third phosphorus-containing catalyst complex to produce adiponitrile.

The 3-pentenenitrile feed to the third reaction zone is obtained from distillation steps described above and typically may comprise at least 95 wt % 3PN, less than 5 wt % of pentenenitriles other than 3PN, and less than 0.1 wt % of the first phosphorus-containing ligand. The 3PN feed may comprise less than 5000 parts per million (ppm), for example, less than 2000 parts per million (ppm), for example, less than 1000 parts per million (ppm), for example, less than 600 parts per million (ppm,) $C_9$ mononitriles.

The HCN feed to the third reaction zone may be a product of the Andrussow process that has been dried by distillation to less than about 250 ppm water, for example, less than 125 ppm water, for example, less than 80 ppm water. However, the HCN feed will usually contain at least some water, since very dry HCN is unstable. Accordingly, the HCN feed may comprise at least 10 ppm, for example, at least 25 ppm, for example, at least 50 ppm, water. The HCN feed to the third reaction zone is preferably substantially free of carbon monoxide, oxygen and ammonia. As an alternative, a cyanohydrin can be used as the source of HCN; see, for example, U.S. Pat. No. 3,655,723.

The third phosphorus-containing catalyst complex generally comprises a transition metal, such as zero-valent nickel, and a monodentate or bidentate phosphorus-containing ligand, which may be the same or different from ligand employed in either the first or the second catalyst complex. The third phosphorus-containing catalyst complex will, however, generally include one or more promoters to enhance the production of dinitriles. As known in the art, promoters influence both catalyst activity and selectivity to the desired ADN. Promoters employed include salts of metals having atomic numbers 13, 21-32, 39-50, and 57-80, for example, zinc, and compounds of the formula $BR'_3$ s wherein R' is an alkyl or an aryl radical of up to 18 carbon atoms, for example triphenylboron. The anions of such metal salts may include halides, for example chloride, sulfates, phosphates, and lower aliphatic carboxylates. Useful promoters are generally known in the art as Lewis acids. In one embodiment, where the Lewis acid promoter is $ZnCl_2$, the mole ratio of promoter to nickel in the third catalyst complex may be in the range of 1:20 to 50:1, for example, from 0.2:1 to 2:1.

The conditions employed in the third reaction zone typically may include a temperature within the range of about 0° C. to about 150° C., for example, within the range of about 25° C. to about 80° C. Generally, the reaction pressure should be sufficient to maintain the HCN in contact with the catalyst dissolved in the liquid reaction mixture. Such pressure is at least, in part, a function of the amount of unreacted HCN present in the reaction mixture. While an upper limit of pressure for this reaction step is not limited to any particular pressure, for practical purposes the pressure generally ranges from about 15 psia to about 300 psia (about 1.03 bar to about 20.7 bar). The overall feed molar ratio of 3PN to HCN to the third reaction zone may be in the range of 1:1 to 100:1, for example, in the range of 1:1 to about 5:1, while the molar ratio of HCN to catalyst may be in the range of 10:1 to 5000:1, for example, 100:1 to 3000:1, for example, in the range 300:1 to 2000:1. The phosphorus-containing ligand used in the reaction of 3PN with HCN is, preferably, a bidentate ligand. The molar ratio of bidentate ligand to nickel in the catalyst for the 3PN hydrocyanation step may be from 1:1 to 10:1, for example, 1:1 to 5:1, for example, 1:1 to 3:1. The residence time in the third reaction zone is typically determined by the desire to obtain a certain degree of conversion of pentenenitriles, HCN, or a combination thereof. In addition to residence time, catalyst concentration and reaction temperature will also affect conversion of reactants to products. Generally, residence times will be in the range of about 0.1 hour to about 30 hours, for example, in the range of about 1 hour to about 20 hours. The HCN conversion may be greater than 99%.

Suitable reactors for the third reaction zone include continuous stirred-tank reactors, loop-type bubble column reactors, gas circulation reactors, bubble column reactors, tubular reactors, or combinations thereof, optionally with apparatus for removing at least a portion of the heat of reaction.

Separation of the Products of the Third Reaction Zone

The reaction product mixture from the third reaction zone is composed mainly of dinitriles, especially the desired adiponitrile (ADN) together with some 2-methylglutaronitile (MGN), pentenenitriles, such as 3PN, 2PN, and (E)-2M2BN, catalyst, catalyst degradation products and promoter. These components may be separated by any method known in the art but typically are treated by a combination of distillation and liquid/liquid extraction steps. For example, one or more stages of distillation may be included between the third reaction zone and a downstream liquid extraction zone to remove lower-boiling constituents, including unreacted 3-pentenenitrile, from the product mixture. The remainder of the product mixture is then fed to a liquid/liquid extraction zone where the mixture is contacted with an extraction solvent. In the extraction zone there is formed an extract phase comprising the extraction solvent and the third catalyst and a raffinate phase comprising adiponitrile, catalyst degradation products and promoter.

The extract phase passes to distillation column, where extraction solvent is separated from the catalyst for recycle back into extraction zone. A catalyst stream is taken from distillation column and is recycled back into the third reaction zone. The raffinate phase may be distilled in one or more distillation steps to separate adiponitrile (ADN) and methylglutaronitrile (MGN) from compounds with a higher boiling point than adiponitrile (ADN) and compounds with a lower boiling point than methylglutaronitrile (MGN) to obtain a first refined dinitrile stream. The first refined dinitrile stream may be further distilled to remove methylglutaronitrile (MGN) from the first refined dinitrile stream to obtain a second refined dinitrile stream enriched in adiponitrile. At least a portion of the second refined dinitrile stream is recycled to the liquid/liquid extraction step as a dinitrile recycle stream.

One embodiment of a representative process for the manufacture of adiponitrile from 1,3-butadiene will now be described with reference to FIG. 1. As shown in the drawing, in the process shown a 1,3-butadiene feed is supplied through line 100 to a first reaction zone $Z_1$, which also receives a supply of hydrogen cyanide through line 120, and a supply of a first phosphorus-containing catalyst complex through line 140. In the first reaction zone $Z_1$ the conditions are controlled so that the 1,3-butadiene reacts with the hydrogen cyanide to produce a reaction product substantially comprising 3-pentenenitrile (3PN) and 2-methyl-3-butenenitrile (2M3BN). A reaction effluent stream is removed from the first reaction zone $Z_1$ through line 122 and is introduced into a separation section 125, to obtain, inter alia, a concentrated catalyst stream 140 and a product stream 200 comprising 2-methyl-3-butenenitrile (2M3BN). The separation section 125 may comprise one or more distillation columns. Unreacted hydrogen cyanide and 1,3-butadiene may also be separated from reaction products and catalyst in separation section 125. Unreacted 1,3-butadiene may be recycled to the first reaction zone $Z_1$ through lines not shown in FIG. 1. A stream comprising 3-pentenenitrile (3PN) may also be withdrawn from separation section 125 through a line not shown in FIG. 1.

A portion of the catalyst separated from reaction products in separation section 125 is recycled to the first reaction zone $Z_1$ through line 140, while a further catalyst portion is removed and fed via line 126 to a liquid/liquid extraction zone 150 to at least partially purify or regenerate the catalyst. A non-polar solvent, such as an alkane, is fed to the liquid/liquid extraction zone 150 through line 130 and a polar solvent, which is immiscible with the non-polar solvent, is also fed to the liquid/liquid extraction zone 150 through line 500. In an alternative embodiment (not shown in FIG. 1), the used catalyst in line 126 and the polar solvent in line 500 are mixed prior to charging the combined stream to extraction zone 150. In extraction zone 150, there is formed a non-polar phase comprising non-polar solvent and catalyst and a polar phase (e.g., a raffinate) comprising polar solvent and, for example, reaction byproducts and catalyst degradation products. The non-polar phase is taken from extraction zone 150 via line 134 and fed to a distillation system 155. The polar phase is taken from extraction zone 150 via line 510 to separation section 1000.

The distillation system 155 is operated to recover the non-polar solvent as an overhead stream which is returned to extraction zone 150 via line 130, optionally with make-up non-polar solvent being added to the overhead stream. Column bottoms from the distillation system 155 comprises partially purified catalyst, which is collected and removed from distillation system 155 through line 156 and introduced at any point for recycle into the first reaction zone $Z_1$. In FIG. 1, partially purified catalyst may be taken from distillation column 155 through line 156 and transferred into line 146 for introduction into catalyst recycle line 140 for recycle into the first reaction zone $Z_1$. FIG. 1 shows the introduction of stream 146 downstream of the take-off stream 126, but this stream may, optionally, be introduced upstream of the take-off stream 126. Optionally, at least a portion of the partially purified catalyst stream in line 156 may be recycled into the second reaction zone $Z_2$. In FIG. 1, partially purified catalyst stream in line 156 may be transferred into line 246 for introduction into catalyst recycle line 240 for recycle into the second reaction zone $Z_2$. Make-up catalyst or catalyst components (additional zero-valent Ni and/or additional phosphorus-containing ligand) may be added to the first and second reaction zones $Z_1$ and $Z_2$ via lines 145 and 245, respectively.

The separation system 1000 conveniently comprises a plurality of distillation columns which separate the reaction byproducts and catalyst degradation products from polar solvent, which is then returned to the extraction zone 150 by line 500.

The 2M3BN-containing product stream 200 separated from reaction products of the first reaction zone $Z_1$ in separation section 125 is introduced into the second reaction zone $Z_2$, which receives a supply of a second phosphorus-containing catalyst complex, which can be the same or different from the first phosphorus-containing catalyst complex, through line 240. In the second reaction zone $Z_2$ the conditions are controlled so that the 2M3BN undergoes isomerization to produce a reaction product comprising substantially 3PN. An effluent stream comprising the second phosphorus-containing catalyst complex and 3PN product is withdrawn from the second reaction zone $Z_2$ via line 222 and is passed into a separation section 225 to obtain, inter alia, a 3PN product stream 300 and a concentrated catalyst stream 240. Separation section 225 may comprise one or more distillation columns.

In the particular embodiment shown in FIG. 1, the second reaction zone $Z_2$ is provided with a second catalyst recovery system for recycling catalyst to the second reaction zone $Z_2$. In this second catalyst recycle system, a portion of the concentrated catalyst stream in line 240 is diverted and fed by line 226 into a liquid/liquid extraction zone 250. A non-polar solvent, such as an alkane, is fed into the liquid/liquid extraction zone 250 through line 230, while a polar solvent, which is immiscible with the non-polar solvent, is also fed into the liquid/liquid extraction zone 250 through line 700. In one embodiment (not shown), the catalyst stream 226 and the polar solvent in line 700 are mixed prior to charging the combined stream to extraction zone 250. In addition, dinitriles from sources not shown in FIG. 1, such as a portion of the refined dinitrile product stream from the third reaction zone $Z_3$, may be added to extraction zone 250, as needed, to accomplish the desired phase separation and extraction.

In extraction zone 250, there is formed a non-polar phase comprising non-polar solvent and catalyst and a polar phase (e.g., a raffinate) comprising, for example, polar solvent, reaction byproducts and certain catalyst degradation products. The non-polar phase is removed from the extraction zone 250 via line 234 and fed to a distillation system 255. The polar phase is removed from the extraction zone 250 and fed via line 710 to a separation section 2000.

The distillation system 255 is operated to recover the non-polar solvent as an overhead stream which is returned to extraction zone 250 via line 230, optionally with make-up non-polar solvent being added to the overhead stream. Column bottoms from distillation system 255 include partially purified catalyst, which may be removed from through line 248 for introduction into catalyst recycle line 240 for recycle into the second reaction zone $Z_2$. Optionally, a side stream may be taken from line 248 into line 247, and this side stream may be used as a catalyst feed to the first reaction zone $Z_1$, for example, by introducing the side stream from line 247 into line 146 or line 140. Any partially purified stream of catalyst, which is subsequently fed to the second reaction zone $Z_2$, may be provided with additional zero-valent Ni and/or phosphorus-containing ligand, for example, via line 245. Although not shown in FIG. 1, line 245 may optionally be fed directly into line 246 or line 248 instead of line 240. Other ways of introducing make-up catalyst are known in the art and may be used.

The separation system 2000 conveniently comprises a plurality of distillation columns which separate the reaction byproducts and catalyst degradation products from polar solvent, which is then returned to the extraction zone 250 by line 700.

Although not shown in FIG. 1, it is possible that the first reaction zone $Z_1$ and the second reaction zone $Z_2$ share a single catalyst recovery system. A shared catalyst recovery system may be desirable when the first and second phosphorus-containing ligands are the same. In such a shared system, the following features may be eliminated or shut down: lines 226, 230, 234, 247, 248, 700, and 710; extraction zone 250; distillation apparatus 255; and separation section 2000. Instead of taking a purge stream via line 226, a purge stream may be taken via line 227 and introduced into line 126 or directly into extraction zone 150. In such a shared catalyst recovery system, any partially purified catalyst stream entering the second reaction zone $Z_2$ would pass through lines 246 and 240 according to the configuration shown in FIG. 1.

The 3PN product separated from reaction products of the second reaction zone $Z_2$ in separation section 225 is introduced via line 300 into the third reaction zone $Z_3$, which also receives a supply of HCN through line 220. 3PN from separation section 125 may also be introduced into the third reaction zone Za through a line or lines not shown in FIG. 1. A third catalyst comprising, for example, zero-valent Ni and a third phosphorus-containing ligand, collectively a third catalyst system, and a Lewis acid promoter is introduced into the third reaction zone $Z_3$ through line 340. The reaction of 3PN and HCN in the third reaction zone $Z_3$ produces a reaction product containing adiponitrile. A reaction product stream is taken from the third reaction zone $Z_3$ by line 400. The reaction product stream comprises, for example, adiponitrile, catalyst, promoter, and unreacted reactants. The reaction product stream may optionally be passed through a separation section (not shown in FIG. 1) to remove unreacted reactants, prior to separation of the catalyst from the adiponitrile product.

Catalyst and adiponitrile product from the product stream in line 400 are passed into liquid/liquid extraction zone 370. A non-polar solvent, such as an alkane, is fed into the liquid/liquid extraction zone 370 through line 330. The non-polar solvent introduced into the liquid/liquid extraction zone 370 may have the same or different composition as the non-polar solvent introduced into the liquid/liquid extraction zone 150. Together, non-polar solvent from line 330 and adiponitrile product from line 400 comprise an extractant system of immiscible components. In extraction zone 370, there is formed a non-polar phase comprising non-polar solvent and catalyst and a polar phase (e.g., a raffinate) comprising adiponitrile, promoter and catalyst degradation products. The non-polar phase is taken from extraction zone 370 via line 334 to a distillation system 375. The polar phase comprising adiponitrile is taken from the extraction zone 370 and fed via line 600 to an adiponitrile purification section 3000.

The distillation system 375 is operated to recover the non-polar solvent as an overhead stream which is returned to extraction zone 370 via line 330, optionally with make-up non-polar solvent being added to the overhead stream. Column bottoms from the distillation system 375 include partially purified catalyst and may be removed from the distillation system 375 through line 340 for recycle to the third reaction zone $Z_3$. Make-up quantities of additional zero-valent Ni and/or third phosphorus-containing ligand along with promoter may be added to the partially purified catalyst in line 340 via line 345.

Adiponitrile purification section 3000 may include, collectively, a series of distillation columns, which provide for the separation of impurities, such as reaction byproducts and catalyst degradation products, from the purified adiponitrile product, which is recovered in line 660. A portion of the purified adiponitrile product may optionally be returned to extraction zone 150 or extraction zone 250 (by lines not shown in FIG. 1) to facilitate phase separation in these extraction zones.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention will now be more particularly described with reference to the following non-limiting Examples.

EXAMPLES

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Comparative Example 1—Synthesis of a Nickel Complex Solution of 2'-(bis(o-tolyloxy)methoxy)-[1,1'-bi(cyclohexan)]-2-yl di-o-tolyl phosphite

Comparative Example 2—Synthesis of a Nickel Complex Solution of Diisopropyl 2,2'-bis((bis(o-tolyloxy)phosphaneyl)oxy)-[1,1'-binaphthalene]-3,3'-dicarboxylate

Comparative Example 3—Isomerization of 2-methyl-3-butenenitrile Using a Nickel Complex Solution of 2'-(bis(o-tolyloxy)methoxy)-[1,1'-bi(cyclohexan)]-2-yl di-o-tolyl phosphite

Comparative Example 4—Isomerization of 2-methyl-3-butenenitrile Using a Nickel Complex Solution of Diisopropyl 2,2'-bis((bis(o-tolyloxy)phosphaneyl)oxy)-[1,1'-binaphthalene]-3,3'-dicarboxylate

Comparative Example 5—Hydrocyanation of 3PN Using a Nickel Complex Solution of 2'-(bis(o-tolyloxy)methoxy)-[1,1'-bi(cyclohexan)]-2-yl di-o-tolyl phosphite

Comparative Example 6—Hydrocyanation of 3PN Using a Nickel Complex Solution of Diisopropyl 2,2'-bis((bis(o-tolyloxy)phosphaneyl)oxy)-[1,1'-binaphthalene]-3,3'-dicarboxylate Experimental Example 1. Synthesis of the nickel complex of Ligand A by a dissolving metal process. In a glove-box having a argon atmosphere, nickel metal powder, 0.33 g, Ligand A, 1.00 g, zinc chloride, 0.05 g, and 3-pentenenitrile, 7.07 g were combined in a 10 mL thick-walled glass vial sealed with a polytetrafluoroethylene lined septum. The solution was stirred with a magnetic stirrer at 60° C. for 24 h to afford solution of the nickel complex of Ligand A in a solution of 3-pentenitrile. The concentration of the nickel complex of Ligand A in solution was measured by high-performance liquid chromatography, and $^{31}P$-NMR spectrometry.

Comparative Example 1-Synthesis. 2'-(bis(o-tolyloxy)methoxy)-[1,1'-bi(cyclohexan)]-2-yl di-o-tolyl phosphite "CEx1" was prepared according to the procedures of WO 99/06357 A1, and the corresponding nickel complex was synthesized following the procedure of Experimental Example 1, but replacing Ligand A for CEx1.

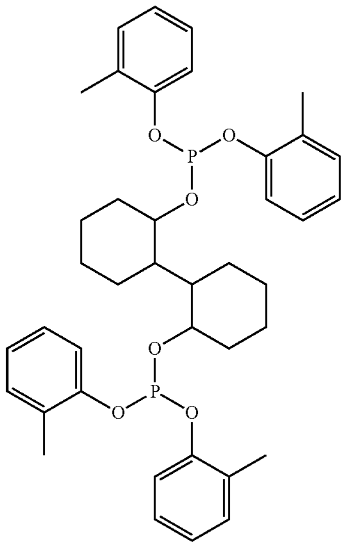 [SMILES: Cc1ccccc1OP(Oc1ccccc1C)OC1CCCCC1C1CCCCC1OP(Oc1ccccc1C)Oc1ccccc1C]

Comparative Example 2-Synthesis. Diisopropyl 2,2'-bis((bis(o-tolyloxy)phosphaneyl)oxy)-[1,1'-binaphthalene]-3,3'-dicarboxylate "CEx2" was prepared according to the procedures of WO 99/06357 A1, and the corresponding nickel complex was synthesized following the procedure of Experimental Example 1, but replacing Ligand A for CEx2.

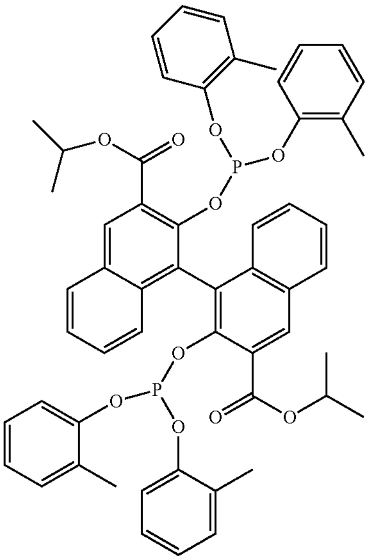 [SMILES: Cc1ccccc1OP(Oc1ccccc1C)Oc1c(C(=O)OC(C)C)cc2ccccc2c1-c1c(OP(Oc2ccccc2C)Oc2ccccc2C)c(C(=O)OC(C)C)cc2ccccc12]

Experimental Example 2. Isomerization of 2-methyl-3-butenenitrile using the nickel complex solution prepared in Experimental Example 1. A portion of nickel catalyst containing solution from Experimental Example 1, 0.50 g, was filtered and was charged to a 5 mL glass serum vial, along with 5.00 g of 2-methyl-3-butenenitrile. The resulting solution was heated to 100° C., and maintained at that temperature for 5 h then cooled to room temperature and was then analyzed by GC within 5 minutes of the conclusion of the experiment. The conversion of 2M3BN was determined to be 84%, and the selectivity to 3-pentenenitriles was 96.5%.

Comparative Example 3-Isomerization of 2-methyl-3-butenenitrile (2M3BN) was performed using the nickel complex of CEx1 following the procedure of Experimental Example 2, but substituting the nickel complex of CEx1 for that of Ligand A. The conversion of 2M3BN was determined to be 80%, and the selectivity to 3-pentenenitriles is 90%.

Comparative Example 4-Isomerization of 2-methyl-3-butenenitrile (2M3BN) was performed using the nickel complex of CEx2 following the procedure of Experimental Example 2, but substituting the nickel complex of CEx2 for that of Ligand A. The conversion of 2M3BN was determined to be 73%, and the selectivity to 3-pentenenitriles is 91%.

Experimental Example 3. Hydrocyanation of 3-pentenenitriles using the nickel complex solution prepared in Experimental Example 1. The mixture was heated in a temperature-controlled aluminum block. HCN was delivered to the flask as liquid feed from a syringe pump. Samples were periodically analyzed by gas chromatography. In the examples presented herein, ADN stands for adiponitrile, MGN stands for 2-methylglutaronitrile, and ESN stands for 2-ethylsuccinonitrile. To a temperature controlled 50 mL glass reaction vessel equipped with a magnetic agitator were added 2.5 grams of the nickel phosphite catalyst solution prepared by the procedure of Experimental Example 1, and 5 mL of 3-pentenenitriles. The mixture was treated with HCN at a nitrogen flow rate of 0.01 mL/min at 70° C. for 1 h. GC analysis of the resulting product mixture indicated an ADN yield of 87.1% and a DN distribution of 91.1%.

Comparative Example 5-Hydrocyanation of 3-pentenenitrile using the nickel complex solution prepared of CEx1 was performed following the procedure of Experimental Example 3, but the nickel complex of Ligand CEx1 was substituted for that of Ligand A. GC analysis of the resulting product mixture indicates an ADN yield of 32% and a DN distribution of 83%.

Comparative Example 6-Hydrocyanation of 3-pentenenitrile using the nickel complex solution prepared of CEx2 was performed following the procedure of Experimental Example 3, but the nickel complex of Ligand CEx2 was substituted for that of Ligand A. GC analysis of the resulting product mixture indicates an ADN yield of 36% and a DN distribution of 67%.

The invention claimed is:

1. A process for the hydrocyanation of an organic compound containing at least one olefinic group comprising reacting the organic compound with hydrogen cyanide in the presence of a catalyst complex comprising a bidentate phosphite ligand and at least one transition metal, wherein the bidentate phosphite ligand comprises a backbone having a structure of acenaphthene-1,2-diol in which the hydrogen atoms of the hydroxyl groups have each been replaced by a $P(OR^1)_2$ group, wherein $R^1$ is an aryl radical optionally substituted with methyl.

2. The process of claim 1, wherein the organic compound comprises 1,3-butadiene.

3. The process of claim 1, wherein the organic compound comprises 3-pentenenitrile.

4. The process of claim 1, wherein each $R^1$ group is an aryl substituted with methyl.

5. The process of claim 1, wherein the bidentate phosphite ligand has the following structure:

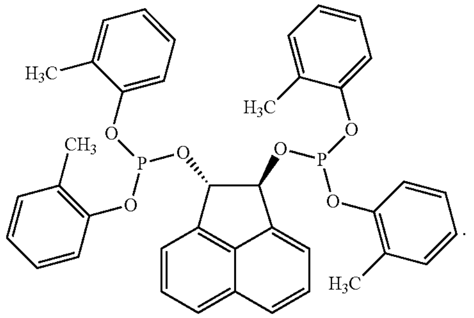 [SMILES: Cc1ccccc1OP(Oc1ccccc1C)O[C@H]1c2cccc3cccc(c23)[C@@H]1OP(Oc1ccccc1C)Oc1ccccc1C]

6. The process of claim 1, wherein the at least one transition metal comprises nickel.

7. The process of claim 1, wherein a product of the hydrocyanation is an unsaturated compound having no more than one carbon-carbon double bond, wherein the process further comprises double bond isomerization of the unsaturated compound having no more than one carbon-carbon double bond comprising contacting the monoethylenically unsaturated compound with the catalyst complex.

8. The process of claim 7, wherein the unsaturated compound having no more than one carbon-carbon double bond comprises 2-methyl-3-butenenitrile.

9. A process for double bond isomerization of an unsaturated compound having no more than one carbon-carbon double bond comprising contacting the compound with a catalyst complex comprising a bidentate phosphite ligand and at least one transition metal, wherein the bidentate phosphite ligand comprises a backbone having a structure of acenaphthene-1,2-diol in which the hydrogen atoms of the hydroxyl groups have each been replaced by a $P(OR^1)_2$ group, wherein $R^1$ is an aryl radical optionally substituted with methyl.

10. The process of claim 9, wherein the compound comprises 2-methyl-3-butenenitrile.

11. The process of claim 9, wherein each $R^1$ group is an aryl substituted with methyl.

12. The process of claim 9, wherein the bidentate phosphite ligand has the following structure:

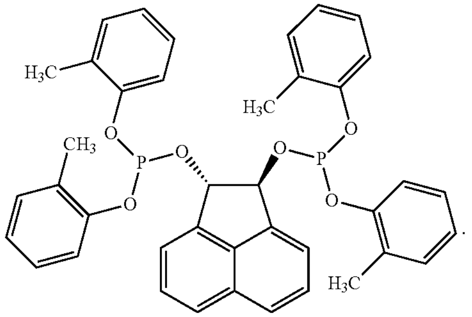 [SMILES: Cc1ccccc1OP(Oc1ccccc1C)O[C@H]1c2cccc3cccc(c23)[C@@H]1OP(Oc1ccccc1C)Oc1ccccc1C]

13. The process of claim 9, wherein the at least one transition metal comprises nickel.

14. A bidentate phosphite ligand comprising a backbone having a structure of acenaphthene-1,2-diol in which the hydrogen atoms of the hydroxyl groups have each been replaced by a $P(OR^1)_2$ group, wherein $R^1$ is an aryl radical optionally substituted with methyl.

15. The bidentate phosphite ligand of claim 14, wherein each $R^1$ group is an aryl substituted with methyl.

16. The bidentate phosphite ligand of claim 14, having the following structure:

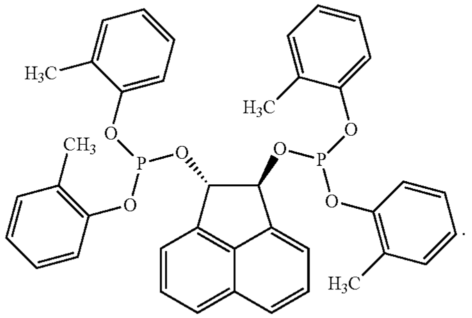 [SMILES: Cc1ccccc1OP(Oc1ccccc1C)O[C@H]1c2cccc3cccc(c23)[C@@H]1OP(Oc1ccccc1C)Oc1ccccc1C]

17. A catalyst complex comprising the bidentate phosphite ligand of claim 14 and at least one transition metal.

18. The catalyst complex of claim 17, wherein the at least one transition metal comprises nickel.

* * * * *